United States Patent [19]

Goldstein

[11] 4,096,589
[45] Jun. 27, 1978

[54] ADJUSTABLE EYE SHADE

[75] Inventor: Morton I. Goldstein, Columbus, Ohio

[73] Assignee: Matrix Groups, Inc., Columbus, Ohio

[21] Appl. No.: 757,621

[22] Filed: Jan. 7, 1977

[51] Int. Cl.² .................................................. A61F 9/00
[52] U.S. Cl. .................................................. 2/12
[58] Field of Search .................. 2/12, 199, 10, 185, 2/DIG. 6

[56] References Cited

U.S. PATENT DOCUMENTS

| 2,019,028 | 10/1935 | Sternberg | 2/12 |
| 2,968,812 | 1/1961 | Vivolo | 2/12 |
| 3,434,469 | 3/1969 | Swift | 2/DIG. 6 |

Primary Examiner—Doris L. Troutman
Attorney, Agent, or Firm—Mahoney & Stebens

[57] ABSTRACT

An adjustable eye shade is provided which includes a headband and detachable visor element. The detachable visor element and headband are provided with hook and loop connecting elements secured at cooperative edge portions which may be selectively interengaged to mount the visor element on the headband at a desired elevation, angled inclination and curvature. The headband may be formed from, or provided at the interiorly facing surface thereof, an absorbent fabric material thereby forming a sweatband for participants in athletic games, such as tennis or golf. The visor element is structurally self-supporting and formed from a flexible material which may be bent or curved into the desired configuration and secured to the forward facing portion of the headband to obtain the desired angle of inclination and curvature for obtaining the most advantageous degree of protection from the sun, the most comfortable position of the headband on the forehead and cosmetic appearance.

7 Claims, 7 Drawing Figures

ADJUSTABLE EYE SHADE

BACKGROUND OF THE INVENTION

Many types of headgear, including visors for protecting the eyes from the sun, have been devised for participants in athletic events. Also, other forms of head gear have been devised which perform the primary function of a sweatband to absorb perspiration from the forehead of the athlete. While many types and forms of such devices have been manufactured and are commercially available, the known devices have generally not proven entirely satisfactory or useful in many instances. One of the primary reasons is that the visor in the known devices are of a fixed configuration that may not be suitable for all persons or for all occasions. An example of one form of headgear designed to meet the objectives, is disclosed in U.S. Pat. No. 2,019,028. That patent discloses a separable headband and visor element. However, the visor is of a fixed configuration and cannot be adjusted to meet different playing conditions.

SUMMARY OF THE INVENTION

An eye shade is provided in accordance with this invention which includes the advantageous feature of adjustability as to the configuration of the visor and relative positioning of the visor on a supporting headband. This headband, in the illustrative embodiment, is designed for wear by participants in athletic events and does not necessarily include an auxiliary head covering. The visor element is formed from a flexible material in sheet form having an inwardly curved edged portion designed to cooperatively interfit and engage with a portion of a headband when the headband is positioned on the wearer's head. Attaching means, or connecting means, is provided to permit the selective interconnecting and positioning of the visor element on the headband at a desired and advantageous relative position.

In accordance with this invention, such connecting means found particularly suitable for this application, is the well-known hook and loop type fabric fasteners which are provided in strip form. One of the elements, either the hook or the loop section, is secured to an outwardly facing portion of the headband and the opposite or mating section of the hook or loop is secured to the peripheral edge or the inwardly curved edge portion of the visor element. Attachment or mounting of the visor element on the headband is conveniently effected through the simple expedient of bending or curving the visor element around a longitudinal axis essentially perpendicular to the inwardly curved edge portion and then pushing that edge into connecting engagement with the cooperative forward edge portions of the headband.

This technique of curving the visor results in an attachment of the visor at an angle of inclination with respect to the headband. Increasing or decreasing the curvature or bending of the visor about this longitudinal axis will obtain a greater or lesser degree of relative inclination to the headband to obtain the most effective and desired protection of the eyes from sun light. Furthermore, mounting the visor on the headband in this manner also enables the wearer to position the headband at the most desired location on the forehead for the particular wearer's comfort and usefulness in the case of the headband also performing the function of the sweatband. This location of the headband on the forehead may not necessarily be the same for the case where the band merely functions as a means of supporting the visor on the wearer's head and that case where the headband must also function as a sweatband. A further objective in variability of curvature and forehead location is providing an advantageous cosmetic appearance which is particularly important to many spectators at athletic events and which spectators may also desire to use an eye shade.

The eye shade of this invention may also be constructed to have an adjustable headband for accommodating different size person's heads with convenience in adjustment. This adjustment may also utilize the hook and loop fabric fastening devices to obtain the greatest degree of adjustment. Also, the headband may be provided with an auxiliary head covering for additional protection of the wearer. Another optional feature of this interconnection of the detachable visor element is that a particular headband assembly may be provided with more than one visor element. The additional visor element may be of greater or less length or width to enable the wearer to better select the particular sun protection that is either desired or required in any particular instance.

These and other objects and advantages of this invention will be readily apparent on the following detailed description of an embodiment thereof and the accompanying drawings which are illustrated of that embodiment.

DESCRIPTION OF THE DRAWING FIGURES

DETAILED DESCRIPTION OF THE ILLUSTRATIVE EMBODIMENT

Figure 1:
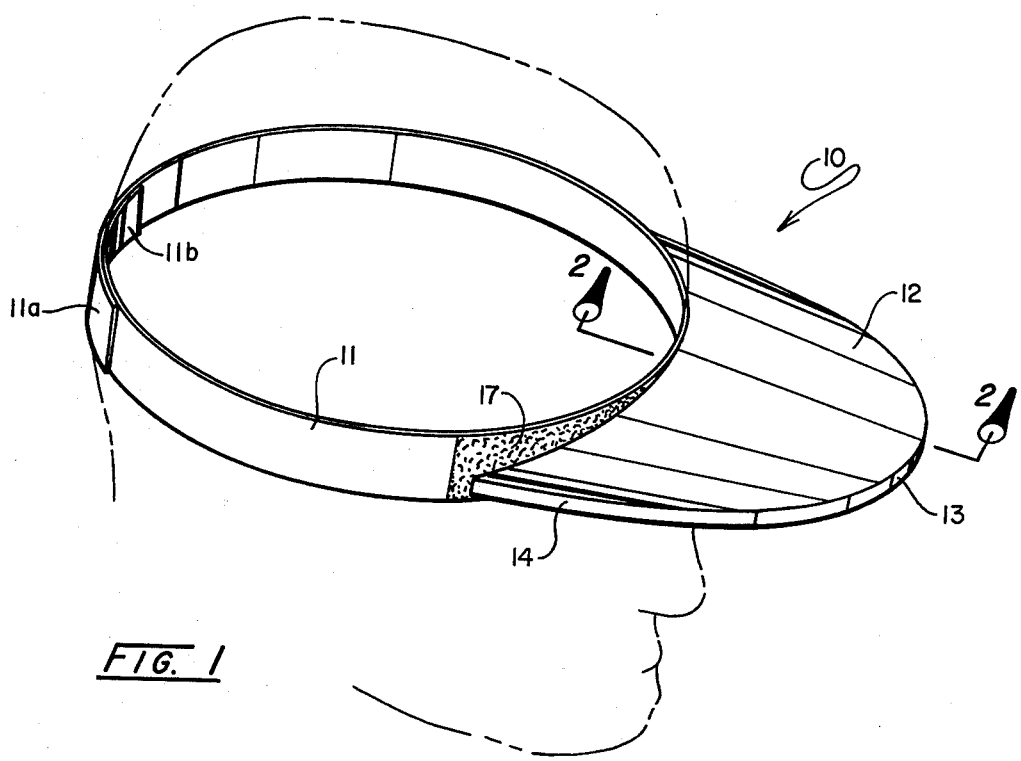
FIG. 1 is a perspective view of the adjustable eye shade embodying this invention and including an assembled headband and visor element as positioned on a wearer's head.
Figure 2:
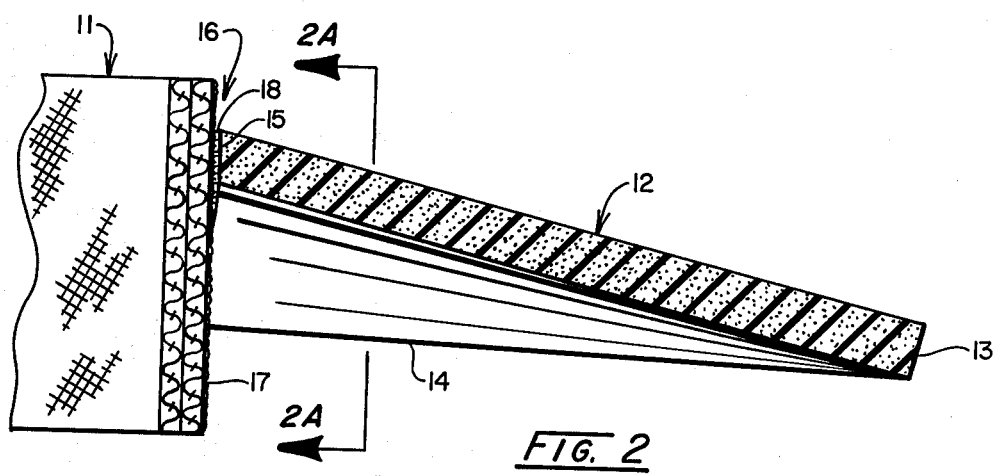
FIG. 2 is a vertical sectional view on an enlarged scale taken along line 2—2 of FIG. 1.

Having reference to FIG. 1, an adjustable eye shade embodying this invention is shown, designated generally by the numeral 10, and is shown positioned on a wearer's head indicated in broken lines for purposes of illustration only. This adjustable eye shade, in accordance with this invention, includes a headband 11 and a visor element 12. In this illustrative embodiment, the headband 11 is designed to also perform a function of a sweatband. As such, the headband is accordingly fabricated from an elongated strip of material that has exceptional ability for absorbing moisture such as perspiration. Preferably, the entire length of the headband will thus be formed from such a material although it will be apparent that only the portions thereof that normally engage or contact the forehead of the wearer may include the high moisture absorbing capability in certain instances. Referring to FIG. 2, it will be noted that this headband 11 is illustrated as being a double layered structure for greater absorbent capacity.

The opposite ends of this strip are of a length to encircle the wearer and overlap a distance at the rear of the head. These overlapping end portions may also advantageously be provided with the hook and loop fastening strips to provide greater versatility and adjustment in adapting the structure to a particular wearer's head. From a dimensional standpoint, the headband 11 may be of the order of 1 to 2 inches in height or transverse dimension to provide the necessary stability and supporting surface for the visor as well as having adequate moisture absorbing capacity.

The visor element 12 is advantageously fabricated from a low density, closed cell, foam material that is formed from a synthetic resinous material. This material is provided in planar sheet form and selection of the closed cell type of foam results in a visor element that is essentially impervious to moisture and non-absorbent. Also, a material of this type is very light weight and thus does not result in an uncomfortably heavy structure.

The configuration of this visor element may be of the conventional shape having a longitudinal axis with a leading edge 13 having the conventional arcuate curvature which is symetrical about the longitudinal axis. This leading edge 13 extends rearwardly at each side where, in the case of a relatively long visor, these sides may be essentially straight line elements 14. Extending between the terminal ends of the straight line elements 14 is an inwardly curved edge adapted to cooperatively interengage with a forwardly facing portion of the headband 11. In this illustrative embodiment, the visor element 12 is formed from the foam material which has a sheet thickness of the order of ⅜ of an inch. This low density foam material is very light weight and in that thickness does not present an excessive weight problem to the wearer. Additionally, the thickness results in a greater edge portion that is available for use in interconnecting the visor element with the headband.

In accordance with this invention, connecting means is provided to permit the selective interconnection or interengagment of the visor element with the headband. Preferably, this connecting means, designated generally by the number 16, is the well known hook and loop fabric fastening elements that are commercially available in strip form for fastening of fabric materials. To effect the desired interconnection, the headband 11 at a forwardly facing portion, is provided with one of the elements while the inwardly curved edge portion 15 of the visor element is provided with the opposite element of the connecting means. In the preferred embodiment, the headband 11 is provided with a strip of the hook element 17 while the visor edge portion is provided with a mating strip of the loop element. This arrangement of the two elements is preferred as a safety precaution since the visor element is detachable and the loop elements are generally incapable of inflicting or causing any injury to the wearer through inadvertant contact with the wearer's face. The strip of fabric having the hook element 17, is of a length to include and extend around the headband to the maximum extent that the visor element may interengage with the band. This maximum extent of coverage would be determined where the visor element remains in the flat planar configuration. Additionally, this strip of the hook element 17 preferably covers the entire vertical surface of the headband for greater versatility and adaptibility to engagement with the visor element which may be disposed in a greater number of vertical positions and different curvatures.

While the visor element 12 is shown having the strip of loop elements 18 extending along the entire edge portion 15, it will be understood that a number of relatively short sections which are spaced along the edge portions may be substituted for economy in manufacture. Three short sections are deemed adequate to perform the connecting function and securely attach the visor element to the headband with one section attached at the midpoint and other two at the opposite ends of the edge.

Both the strips of hook and loop elements 17 and 18 may be secured to the respective headband or visor element by simple fastening means such as sewing and stitching or adhesive bonding. The particular type of attachment will be determined from the particular material utilized in fabrication of the respective elements. Also, while the headband is illustrated as being fabricated from a material other than either the fabric strips of either hook or loop elements, it will be understood that the entire headband itself may comprise a strip of either the hook or loop elements as may be appropriate. Such a construction would promote uniformity of appearance or simplify manufacture, or both.

Figure 2A:
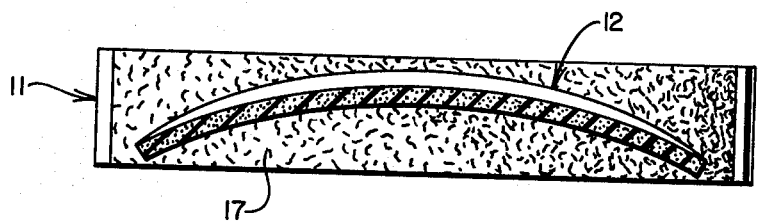
FIG. 2A is a vertical sectional view on a reduced scale taken along line 2A—2A of FIG. 2.

Assembly of the visor element with the headband is easily and readily accomplished to achieve the desired configuration for the visor element and angular relationship to the headband. This assembly is accomplished by first curving the visor element about its longitudinal axis, which axis is essentially represented by the section line 2—2 in FIG. 1, to displace the edge portions at the straight line elements 14 in relatively downward relationship to the normal horizontal plane of the material. This results in a downwardly curved channel configuration which, when the visor is held in this position and the inwardly curved edge portion 15 carrying the loop elements 18 pushed into interengaging relationship with the hook elements on the headband, will be the retained curvature shown in FIG. 2A. Additionally, this downward curvature of the visor about the longitudinal axis in cooperation with the curvature of the headband, which conforms to the wearer's head, will result in the visor element assuming a downwardly inclined angular relationship to the headband. This is illustrated in FIG. 2 and where it will be noted that the inwardly curved edge portion 15 will accommodate to the angular inclination through the interengagement of the relatively flexible hook and loops elements 17 and 18. Since the hook and loop elements are formed from a flexible material, this edge portion will readily adapt to the angle of inclination whereby the visor element will be retained in the desired curvature and angular relationship. It will also be noted with reference to FIG. 2, that the visor element may also be otherwise positioned vertically, either higher or lower than that illustrated, for greater versatility in adjustment of the assembled eye shade.

Figure 3:
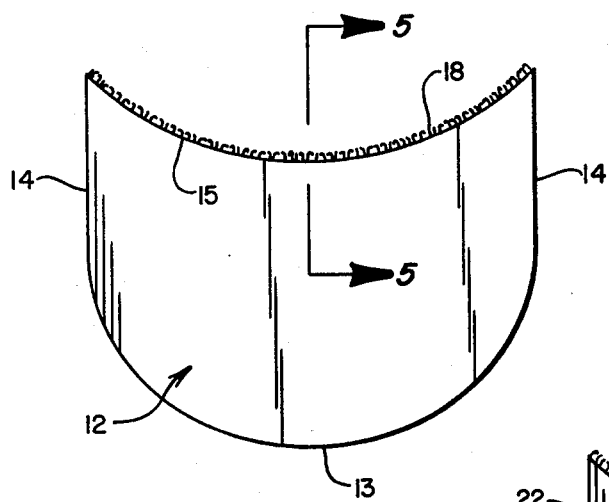
FIG. 3 is a plan view of the visor element shown in FIG. 1 detached from the headband.
Figure 4:
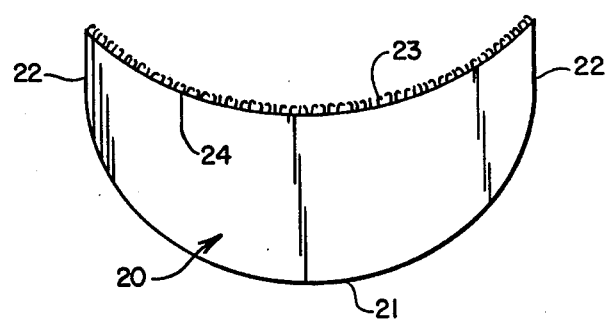
FIG. 4 is a plan view of a modified visor element having a relatively shorter longitudinal length.
Figure 5:
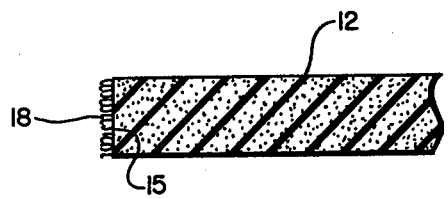
FIG. 5 is a fragmentary vertical sectional view on an enlarged scale taken along line 5—5 of FIG. 3.

FIG. 4 is illustrative of a modified form or configuration for a visor element. This modified visor element is designated by the numeral 20 and is seen to be relatively shorter in longitudinal length when compared with the visor element shown in FIGS. 1 and 3. However, this visor element 20 is also formed with a forward curved edge portion 21 which terminates in relatively short, straight line elements 22 at each side. A strip of loop elements 23 are secured to an inwardly curved edge portion 24 extending between the terminal ends of the side elements 22. It will be readily apparent that the visor element may be conveniently fabricated in various other configurations as may be determined necessary or advantageous for particular applications.

Figure 6:
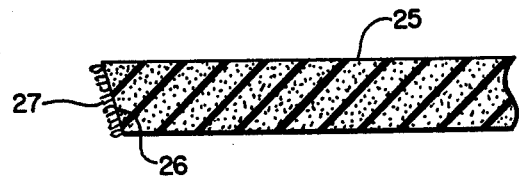
FIG. 6 is a vertical sectional view of a visor element similar to FIG. 5 but having a modified peripheral edge portion.

FIG. 6 is illustrative of a modified curved edge portion configuration of a visor element which carries the strip of loop elements. In FIG. 6, the visor element is generally designated by the numeral 25 with the edge portion designated 26. In this modified structure, the edge portion 26, is initially formed to have a relative angularly disposed relationship to the main body of the visor element. The reason for this angular relationship is that the visor element will then more readily accommodate to greater angle of attachment with respect to the headband. Again, the connecting means includes the loop element strip, indicated by the numeral 27, that may be adhesively bonded to the edge portion 26.

Further variation in the angularly disposed relationship of the visor to the headband can be accomplished by forming a visor with an inwardly curved edge portion having a radius of curvature that is different from that illustrated in either FIG. 3 or 4. Increasing or decreasing the radius of curvature from that illustrated in either FIG. 3 or 4 will result in a proportional decrease or increase in the degree of angular inclination that can be obtained with a specific visor.

Having thus described the illustrative embodiments of an adjustable eye shade incorporating the advantageous features of this invention, it will be readily seen that such an eye shade is particularly capable of performing the primary and desired function of providing protection from the sunlight as to the wearer's eyes. This structure is readily adjusted to the personal preferred configuration of the wearer and is capable of accommodating the particular problems encountered at any instant of use. Mounting of the headband on the wearer's head is readily accomplished and the headband can be adjusted to permit positioning at a desired location. The detachable interconnection of the visor element with respect to the headband, produces the required curvature and angle of inclination with respect to the headband and the front of the wearer's face, for optimum shielding from the sunlight. It will also be readily seen that providing of an eyeshade assembly which includes two or more visor elements that are of different configuration, greatly enhances the versatility of the eyeshade as to a particular person's requirements.

Also, having thus described the basic illustrative embodiments, it will be readily apparent that other modifications may be easily improvised to achieve various desired objectives within the scope of this invention. In addition to the modifications previously indicated, one other such modification relates to the construction of the headband. The headband, as indicated, may be incorporated with or formed as a part of the head covering (not shown) and as such, may be formed of other materials. Additionally, the headband may be provided with other forms of adjustment or elimination of adjustment may be accapted in certain instances. Furthermore, the headband may be formed from a non-absorbent material but provided with a detachable throw-away absorbing element at desired portions. In addition to the illustrated configurations of the visor element, the edge portion may be otherwise configurated or auxiliary elements may be included to further alter the angle of inclination when attached to the headband. Such other and various modifications will be readily apparent to the skilled artisan and enable one to construct an adjustable eyeshade, having the desired advantageous characteristics and features. One such further modification and adaptation of the invention is that for purposes of cosmetic appearance, particularly in the case of spectators, the visor may be covered with decorative fabric.

It is also contemplated that an eye shade embodying this invention will be provided as a set comprising a headband and several differently configured visors. For example, in the case of an active player in an athletic event, a headband of high persperation absorabency would be provided along with a plurality of visors that may be of different lengths, different widths, different radii of curvature for the inwardly curved edge portion, or perhaps different colors. With such a set arrangement, the player can readily and quickly exchange one visor for another during play without significant interruption of the game. The variations obtainable as to each particular visor would be complementary to the other visors in a set and thus provide a very wide range of adjustability. The visors being compact and lightweight permits carrying of one or more in a packet. Also, the absorbent headband can be worn without a visor but the visor being retained in the player's pocket for use as desired.

It will be readily apparent that a particularly novel and advantageous adjustable eye shade is provided by this invention. This eye shade structure incorporating a detachable headband and visor assembly wherein the visor may be flexed to a desired curvature and attached to the headband enables the wearer to obtain the desired degree of curvature and angular inclination relative to the headband. Additionally, the headband may be selectively positioned on the wearer's forehead at a position that is the most comfortable and, in the case of an eye shade for an active sports participant, provide optimum shielding from the sun.

Having thus described this invention, what is claimed is:

1. An adjustable eye-shade comprising
   a head band positionable in retained relationship on a person's head,
   a visor element of flexible material forming an eye-shading panel, said panel having a peripheral edge which includes an inwardly curved portion that is adapted to cooperatively interfit with said headband, and
   connecting means for selectively interconnecting said peripheral edge of said visor element to said headband, said connecting means being a two element structure wherein one of said elements includes a loop surface and the other a hook surface which are cooperatively interengageable for subsequent disengagement, one element of said connecting means fastened to said headband at an exteriorally facing surface thereof and the other element secured to the inwardly curved peripheral edge portion of said visor element.

2. An adjustable eye-shade according to claim 1 wherein said headband has a vertical dimension substantially greater than the thickness of said visor element.

3. An adjustable eye-shade according to claim 1 wherein the inwardly curved peripheral edge portion of said visor element is inwardly inclined in downward relationship to an upper surface thereof.

4. An adjustable eye-shade according to claim 1 wherein the loop surface element of said connecting means is attached to said visor element and the hook surface element is attached to said headband.

5. An adjustable eye-shade according to claim 1 wherein said visor element is formed from a low-density, closed cell synthetic-foam resin material.

6. An adjustable eye-shade according to claim 5 wherein said visor element is a panel of the order of $\frac{3}{8}$ inch in thickness.

7. An adjustable eye-shade according to claim 1 wherein said connecting means is adhesively bonded to the respective headband and visor element.

* * * * *

Notice of Adverse Decision in Interference

In Interference No. 100,796, involving Patent No. 4,096,589, M. I. Goldstein, ADJUSTABLE EYE SHADE, final judgment adverse to the patentee was rendered Mar. 4, 1983, as to claims 1 and 2.

[*Official Gazette June 14, 1983.*]